United States Patent
Carter

(10) Patent No.: US 7,855,311 B2
(45) Date of Patent: Dec. 21, 2010

(54) FORMATION OF HYDROXYCARBONYL COMPOUNDS

(76) Inventor: Melvin K. Carter, 2300 Sutter View La., Lincoln, CA (US) 95648

( * ) Notice: Subject to any disclaimer, the term of this patent is extended or adjusted under 35 U.S.C. 154(b) by 0 days.

(21) Appl. No.: 12/382,148

(22) Filed: Mar. 10, 2009

(65) Prior Publication Data

US 2010/0234644 A1  Sep. 16, 2010

(51) Int. Cl.
*C07C 45/72* (2006.01)
(52) U.S. Cl. .................. 568/388; 568/392; 568/463
(58) Field of Classification Search ............... 568/463, 568/881, 388, 392
See application file for complete search history.

(56) References Cited

U.S. PATENT DOCUMENTS

| 4,017,537 | A  | * | 4/1977 | McCollum et al. | 260/494 |
| 4,247,653 | A  | * | 1/1981 | Wagner | 521/158 |
| 6,090,986 | A  | * | 7/2000 | Godwin et al. | 568/451 |
| 6,552,232 | B2 | * | 4/2003 | Mehnert et al. | 568/463 |
| 6,586,636 | B2 | * | 7/2003 | Kelly | 568/463 |

* cited by examiner

*Primary Examiner*—Sikarl A Witherspoon

(57) ABSTRACT

Aldehyde and ketone reactants are converted to hydroxyaldehydes, polyhydroxyaldehydes, hydroxyketones and/or polyhydroxyketones in liquid phase by an aldol condensation process where a selected product carbon chain length is produced using specific concentrations of soluble inorganic base at sub-ambient temperature.

8 Claims, No Drawings

FORMATION OF HYDROXYCARBONYL COMPOUNDS

BACKGROUND

1. Field of Invention

Aldehydes and ketones have been reported to be chemically converted to hydroxyaldehydes, polyhydroxyaldehydes, hydroxyketones and/or polyhydroxyketones in the presence of acids, neutral ionic species and/or bases. A number of reactions have been disclosed for formation of products at elevated temperatures, long reaction times and predominantly low conversion efficiencies but formation of products of controlled molecular weight or carbon-carbon chain length has not been taught. The invention taught in this application is chemical conversion of aldehydes, containing two or more carbon atoms, to products of selected carbon chain length using inorganic bases in a specific concentration range at sub-ambient temperatures. In addition ketones have been catalytically converted to solid products.

The subject of this application is a key step in the catalytic chemical conversion sequence of cellulose to ethanol, ethanol to acetaldehyde then to polyhydroxy aldehydes of specific molecular weight for final conversion to aliphatic hydrocarbons, namely gasoline by methanation or hydrogenation. By forming hydroxyaldehyde or hydroxyketone products of selected molecular weight in substantial yields gasoline can be produced from natural renewable products grown in this country without the expensive refining process and without the need for petroleum.

2. Description of Prior Art

The chemical and fuel processing industries have grown to maturity using petroleum feed stocks. Petroleum is a non-renewable, depleting resource that may become unavailable in the next 100 years. This planet Earth fosters continual growth of numerous carbohydrate based plants including trees, grasses, grains, fruits and vegetables plus their supporting cellulosic plant stalks and related natural waste materials for recycle. Grains, corn cobs, prairie grasses and other cellulosic materials are subject to bio-fermentation, thermal and catalytic processes producing ethanol and related products. A major industry is rapidly developing in ethanol production and much of the product is sold as combustion engine fuel or its additive. Ethanol is becoming more available as a renewable resource and this application teaches conversion of aldehydes, including acetaldehyde derived from ethanol to valuable intermediates for use in production of gasoline and industrial chemical intermediates.

The invention disclosed in this application teaches chemical conversion of aldehydes containing two or more carbon atoms and ketones to products of selected molecular weight of hydroxyaldehydes, polyhydroxyaldehydes, hydroxyketones and/or polyhydroxyketones in liquid phase using a specific concentration range of soluble inorganic base. This process provides a method for production of concatenated carbon-carbon backbone reactive molecules of predetermined chain length. For example, $C_2$ reactant aldehydes, such as acetaldehyde, are converted to $C_4$ through $C_8$ for a dilute base, $C_8$ through $C_{12}$ for a slightly more concentrated base and $C_{12}$ through $C_{30}$ for more concentrated base. Such concatenated carbon-carbon backbone molecules become a basis for manufacture of hydrocarbon fuels and industrial chemical intermediates by means of a reduction process. For example, the concentration range of $C_8$ through $C_{12}$ affords direct conversion to gasoline fuel.

There are a number of hot tube gas reactions reported for preparation of low concentrations of hydroxyaldehydes, hydroxyketones and/or unsaturated aldehydes conducted by passing aldehyde or ketone vapors over supported catalysts at elevated temperature. There are also some slower liquid phase reactions producing much less than a majority of products. U.S. Pat. No. 6,586,636, issued Jul. 1, 2003, introduced a process for preparation of unsaturated aldehydes from straight chain $C_3$, $C_4$ or $C_6$ vaporized aldehydes on a catalyst at 175° C. to 350° C. U.S. Pat. No. 6,552,232, issued Apr. 22, 2003, disclosed preparation of aldol products from aldehydes in ionic medium on supported base catalyst at −20° C. to 300° C., preferably 80° C. to 90° C. in a period of three hours at pressures of 1 atmosphere to 1000 atmospheres. This application makes use of neutral ionic liquid media and a basic catalyst where the ionic liquid medium is selected from 1-butyl-3-methyl imidazolium, 1-butyl-2,3-dimethyl imidazolium, 1-butyl-pyridinium, pyridinium or imidazolium species, and derivatives thereof, $BF_4$ ion and $PF_6$ ion species as well as basic catalyst comprising hydroxide species. U.S. Pat. No. 6,090,986, issued Jul. 18, 2000, discussed formation of esters from $C_9$ alcohols formed from a $C_6$ aldehyde and propanal by an aldol process producing >35% product then hydrogenating the unsaturated aldehyde to a saturated $C_9$ aldehyde. U.S. Pat. No. 4,017,537, issued Apr. 12, 1977, taught preparation of aldol products from aldehydes with the aid of an esterfying agent at 150° C. to 280° C. U.S. Pat. No. 4,247,653, issued Jan. 27, 1981, discussed formation of up to 40% hydroxyaldehyde products from formaldehyde in a temperature range of 10° C. to 150° C. There are also a number of records of prior art disclosing application of supported transition metal catalysts for both formation of aldehydes and for their reaction to products at elevated temperatures and pressures by means of an aldol condensation process. These reactions appear to be slow and do not teach formation of products of a controlled carbon-carbon chain length useful for gasoline production of other specific range hydrocarbon formation.

The invention taught in this application is chemical conversion of aldehydes, containing two carbon atoms or more, to products comprising hydroxyaldehydes and/or polyhydroxyaldehydes of controlled carbon chain length using selected concentrations of soluble inorganic bases at sub-ambient temperatures. This application also teaches catalytic conversion of ketones to products comprising hydroxyketones and/or polyhydroxyketones.

It is an object of this invention, therefore, to provide chemical conversion of aldehydes, containing two carbon atoms or more, to products comprising hydroxyaldehydes and/or polyhydroxyaldehydes of controlled carbon chain length using selected concentrations of soluble inorganic bases at sub-ambient temperatures. It is another object of this invention to teach sub-ambient conversion of acetaldehyde reactants to products comprising 3-hydroxybutyraldehyde ($C_4$) using 0.0005 g/mL of soluble base, 3-hydroxybutyraldehyde and 3,5-dihydroxyhexeraldehyde ($C_4$ and $C_6$) using 0.004 g/mL of soluble inorganic base, $C_6$ to $C_{14}$ using 0.03 g/mL of soluble base, $C_{12}$ to $C_{32}$ using 0.05 g/mL of soluble base and greater than $C_{100}$ using 0.3 g/mL of the soluble portion of inorganic bases comprising sodium, lithium, potassium, rubidium, cesium, magnesium, calcium, barium, strontium hydroxides, carbonates, bicarbonates and/or phosphates. It is still another object of this invention to teach catalytic conversion of ketones to hydroxyl ketones and polyhydroxy ketones. Other objects of this invention will be apparent from the detailed description thereof that follows, and from the claims.

SUMMARY OF THE INVENTION

The invention disclosed in this application teaches chemical conversion of aldehydes, containing two carbon atoms or more, comprising acetaldehyde, propionaldehyde and butyraldehyde to hydroxyaldehydes and polyhydroxyaldehydes products of selected molecular weight using specific concentrations of inorganic bases. In addition, it teaches catalytic conversion of ketones comprising acetone and methyl ethyl ketone to products of hydroxyketones and/or polyhydroxyketones using inorganic bases.

DETAILED DESCRIPTION OF THE INVENTION

Published patents teach that aldehydes in contact with strong base can form polyhydroxy aldehyde oligomers of an uncontrolled chain length. Prior patent applications describe aldehyde reactions in strong base but do not teach formation of products of controlled chain length. The present application teaches formation of polyhydroxy aldehydes of specific chain lengths by reacting aldehydes of two carbon atoms or more in the presence of a base of a selected concentration. For example, butyraldehyde forms oligomers comprising a range of $C_{12}$ to $C_{28}$, propionaldehyde forms oligomers comprising a range of $C_9$ to $C_{21}$ and acetaldehyde forms oligomers comprising a range of $C_6$ to $C_{14}$ as determined by the concentration of base, in this case 0.03 g/mL. This latter range of ethanol based acetaldehyde products is quite useful because they can be readily converted to gasoline without the need for petroleum or distillation.

Aldehydes are readily converted to polyhydroxy aldehydes but by contrast ketones do not form dimers or oligomers except when in contact with a transition metal catalyst and a strong base. This contrasts with older chemical literature that suggests ketones may also form polyhydroxy ketones by the aldol oligomerization process in the absence of a transition metal catalyst. The present application teaches catalytic oligomerization of ketones in contact with a strong base.

Chemical conversion of aldehydes, containing two carbon atoms or more, to products comprising hydroxyaldehydes and/or polyhydroxyaldehydes, and ketones to products comprising hydroxyketones and/or polyhydroxyketones of selected carbon-carbon chain length using specific concentrations of soluble inorganic bases is taught in this application. For example, acetaldehyde produced products comprising 3-hydroxybutyraldehyde ($C_4$) using 0.0005 g/mL of soluble base, 3-hydroxybutyraldehyde and 3,5-dihydroxyhexanaldehyde ($C_4$ and $C_6$) using 0.004 g/mL of soluble inorganic base, $C_6$ to $C_{14}$ using 0.03 g/mL of the soluble portion of inorganic bases comprising sodium, lithium, potassium, rubidium, cesium, magnesium, calcium, barium, strontium, carbonates, bicarbonates, phosphates and/or borates at temperatures in the −25° C. to 20° C. range. Propionaldehyde produced products comprising 4-hydroxybutyraldehyde and 4,7-dihydroxynonanaldehyde ($C_6$ and $C_9$) using 0.004 g/mL of soluble inorganic base, $C_6$ to $C_{15}$ using 0.03 g/mL of soluble base. Butyraldehyde produced products comprising 5-hydroxybutyraldehyde and 5,9-dihydroxydodecanaldehyde ($C_8$ and $C_{12}$) using 0.004 g/mL of soluble inorganic base, $C_8$ to $C_{20}$ using 0.03 g/mL of soluble base.

A series of aldol condensation reactions was conducted in aqueous liquid phase at 0° C. to 15° C. by varying the concentration of sodium hydroxide. Hydroxide concentration was adjusted to control the degree of oligomerization such that aldol formation was, in most cases, rapid and exothermic. Ketones comprising acetone and methyl ethyl ketone have been converted to liquid and solid products. A number of examples of specific product formation from acetaldehyde, propionaldehyde and butyraldehyde as well as acetone and methyl ethyl ketone are presented here.

Example 1

A 1.0 mL sample of butyraldehyde was stirred with 3.0 g of NaOH dissolved in 10 mL of water for 5 minutes at 10° C. The product was extracted with hexane solvent producing 0.985 g of product or 98% viscous oily oligomers comprising a range up to $C_{100}$.

Example 2

A 1.0 mL sample of butyraldehyde was stirred with 0.5 g of NaOH dissolved in 10 mL of water for 5 minutes at 14° C. The product was extracted with dichloromethane solvent producing 0.842 g of product or 84% oily oligomers comprising a range up to $C_{48}$.

Example 3

A 1.0 mL sample of butyraldehyde was stirred with 0.3 g of NaOH dissolved to make 10 mL of solution for 5 minutes at 11° C. The product was an opaque, colorless oil and was extracted with ethyl acetate solvent producing 0.720 g or 72% viscous oily oligomers comprising a range up to $C_{28}$.

Example 4

A 1.0 mL sample of butyraldehyde was stirred with 0.04 g of NaOH dissolved to make 10 mL of solution for 5 minutes at 4° C. Product was white, opaque suspension and was extracted with ethyl acetate solvent producing 0.585 g or 58% liquid oligomers comprising a range of $C_8$ to $C_{12}$.

Example 5

A 1.0 mL sample of propionaldehyde was stirred with 3.0 g of NaOH dissolved to make 10 mL of solution for 5 minutes at 13° C. Initial product was a light yellow oil that formed 0.94 g liquid and ~0.08 g clear colorless crystals. The product was extracted with ethyl acetate solvent producing 100% of oily oligomers comprising a range up to $C_{150}$.

Example 6

A 1.0 mL sample of propionaldehyde was stirred with 0.5 g of NaOH dissolved to make 10 mL of solution for 5 minutes at 12° C. The product was extracted with ethyl acetate solvent producing 0.688 g of a light oily product or 68% oligomers comprising a range up to $C_{45}$.

Example 7

A 1.0 mL sample of propionaldehyde was stirred with 0.3 g of NaOH dissolved to make 10 mL of solution for 5 minutes at 10° C. Product was opaque, white suspension. Product was extracted with ethyl acetate producing 0.505 g, 50% oligomers comprising a range up to $C_{21}$.

Example 8

A 1.0 mL sample of propionaldehyde was stirred with 0.04 g of NaOH dissolved to make 10 mL of solution for 5 minutes at 10° C. Initial product was a clear, colorless solution that changed in time. It was extracted with ethyl acetate solvent after one hour producing 1.00 g liquid or 100% oligomers comprising a range of $C_6$ to $C_9$.

Example 9

A 1.0 mL sample of acetaldehyde was stirred with 3.0 g of NaOH dissolved to make 10 mL of solution for 5 minutes at 13° C. Product was a yellow turbid dispersion. Product was extracted immediately with ethyl acetate solvent producing 0.55 g or 55% oligomers comprising a range of products up to $C_{250}$.

Example 10

A 1.0 mL sample of acetaldehyde was stirred with 0.5 g of NaOH dissolved to make 10 mL of solution for 5 minutes at 14° C. Product was clear yellow after 10 minutes and became turbid after 24 minutes. Product was extracted with ethyl acetate solvent producing 0.198 g or 19% oligomers comprising a distribution of products from $C_{12}$ to $C_{32}$.

Example 11

A 1.0 mL sample of acetaldehyde was stirred with 0.3 g of NaOH dissolved to make 10 mL of solution for 5 minutes at 13° C. Product was clear, colorless and became clear, light yellow after 30 minutes. Product was extracted with ethyl acetate solvent producing 0.070 g or 7% oligomers comprising a distribution of products from $C_6$ to $C_{14}$.

Example 12

To the teflon cup liner of a 23 mL Parr stainless steel reactor were added 0.059 g of a dry Co(II,III) catalyst (prepared by reacting 0.0229 g tetrachlorocatechol plus 0.0049 g sodium carbonate in 3 g water with 0.0110 g of cobalt (II) chloride hexahydrate and adding to the product produced from 0.0385 g tetrachlorocatechol plus 0.0085 g sodium carbonate in 3 g water reacted with 0.0124 g cobalt (III) hexamine chloride with heating and stirring), 1.05 g NaOH and 6.00 g acetone. The Teflon cap was put in place, the reactor sealed and wrapped with an electric heating tape. Heating at 140° C. for 55 minutes produced 53% red brown liquid product and 47% brown oily solid product in an essentially quantitative yield.

Example 13

To the teflon cup liner of a 23 mL Parr stainless steel reactor were added 0.0279 g of dry cobalt sulfate, 1.03 g solid sodium hydroxide and 6.01 g methyl ethyl ketone. The Teflon cap was put in place, the reactor sealed and wrapped with an electric heating tape. Heating at 250° C. for 59 minutes produced 0.313 gram or 5.2% of a colorless solid gel product.

What is claimed is:

1. A process for preparation of products comprising $C_4$ hydroxyaldehydes to $C_{250}$ polyhydroxyaldehydes by rapidly mixing acetaldehyde with inorganic base in a concentration range comprising 0.0005 g/mL to 0.5 g/mL at greater than pH=10 at a temperature of −25° C. to 20° C. until completed.

2. A process for preparation of products comprising $C_4$ hydroxyaldehydes to $C_{250}$ polyhydroxyaldehydes by rapidly mixing acetaldehyde with inorganic base comprising alkali metal or alkaline earth hydroxides, carbonates, bicarbonates, phosphates and/or borates in a concentration range comprising 0.0005 g/mL to 0.5 g/mL, at greater than pH=10 at a temperature of −25° C. to 20° C. until completed.

3. A process for preparation of products comprising 3-hydroxybutyraldehyde ($C_4$), 4-hydroxyhexanaldehyde ($C_6$) or 5-hydroxyoctanaldehyde ($C_8$) by rapidly mixing acetaldehyde, priopionaldehyde or butyraldehyde respectively with inorganic base comprising alkali metal or alkaline earth hydroxides, carbonates, bicarbonates, phosphates and/or borates at a concentration of 0.0005 g/mL at greater than pH=10 at a temperature of −25° C. to 20° C. until completed.

4. A process for preparation of products comprising polyhydroxyaldehydes of molecular carbon chain length comprising $C_4$ to $C_6$, $C_6$ to $C_9$ or $C_8$ to $C_{12}$ by rapidly mixing acetaldehyde, priopionaldehyde or butyraldehyde respectively with inorganic base comprising alkali metal or alkaline earth hydroxides, carbonates, bicarbonates, phosphates and/or borates at a concentration of 0.004 g/mL at greater than pH=10 at a temperature of −25° C. to 20° C. until completed.

5. A process for preparation of products comprising polyhydroxyaldehydes of molecular carbon chain length comprising $C_6$ to $C_{14}$, $C_9$ to $C_{21}$ or $C_{12}$ to $C_{28}$ by rapidly mixing acetaldehyde, priopionaldehyde or butyraldehyde respectively with inorganic base comprising alkali metal or alkaline earth hydroxides, carbonates, bicarbonates, phosphates and/or borates at a concentration of 0.03 g/mL at greater than pH=10 at a temperature of −25° C. to 20° C. until completed.

6. A process for preparation of products comprising polyhydroxyaldehydes of molecular carbon chain length comprising $C_{12}$ to $C_{32}$, $C_{18}$ to $C_{48}$ or $C_{24}$ to $C_{64}$ by mixing acetaldehyde, priopionaldehyde or butyraldehyde respectively with inorganic base comprising alkali metal or alkaline earth hydroxides, carbonates, bicarbonates, phosphates and/or borates at a concentration of 0.05 g/mL at greater than pH=10 at a temperature of −25° C. to 20° C. until completed.

7. A process for preparation of products comprising polyhydroxyaldehydes of molecular carbon chain length greater than $C_{100}$ by mixing reactants comprising acetaldehyde, priopionaldehyde or butyraldehyde with inorganic base comprising alkali metal or alkaline earth hydroxides, carbonates, bicarbonates, phosphates and/or borates at a concentration of 0.3 g/mL at greater than pH=10 at a temperature of −25° C. to 20° C. until completed.

8. A process for preparation of products comprising hydroxyketones and polyhydroxyketones by chemically condensing reactants comprising acetone or methyl ethyl ketone with inorganic base comprising alkali metal or alkaline earth hydroxides, carbonates, bicarbonates, phosphates and/or borates at greater than pH=10 and a transition metal catalyst of bi-metal, tri-metal and/or poly-metal backbone or molecular string type compound comprising cobalt (II) sulfate, cobalt (II) tetrachlorocatechol or iron (II) oxalate in a sealed reactor at temperatures up to 250° C.

* * * * *